United States Patent [19]

French

[11] Patent Number: 4,800,900
[45] Date of Patent: Jan. 31, 1989

[54] EXTERNAL STRAP INCONTINENCE CONTROL DEVICE

[75] Inventor: Gerald J. French, Spencer, Ind.

[73] Assignee: Vance Products, Inc., Spencer, Ind.

[21] Appl. No.: 101,078

[22] Filed: Sep. 25, 1987

Related U.S. Application Data

[63] Continuation-in-part of Ser. No. 926,955, Nov. 4, 1986, abandoned.

[51] Int. Cl.$^4$ .......................................... A61M 19/00
[52] U.S. Cl. .......................... 128/885; 128/DIG. 25; 128/327; 600/31
[58] Field of Search ............... 128/1 R, DIG. 25, 346, 128/326, 327

[56] References Cited

U.S. PATENT DOCUMENTS

| | | | |
|---|---|---|---|
| 2,455,859 | 12/1948 | Foley | 128/346 |
| 2,533,924 | 12/1950 | Foley | 128/346 |
| 2,581,114 | 1/1952 | Larson | 128/79 |
| 2,756,753 | 7/1956 | Means | 128/346 |
| 3,155,096 | 11/1964 | Outwin | 128/346 |
| 3,203,421 | 8/1965 | Bialick | 128/346 |
| 3,495,589 | 2/1970 | Clement | 128/79 |
| 3,586,001 | 6/1971 | Sanderson | 128/327 |
| 3,866,611 | 2/1975 | Baumrucker | 128/346 |
| 4,384,583 | 5/1983 | Speelman et al. | 128/327 |
| 4,428,365 | 1/1984 | Hakky | 128/1 R |

FOREIGN PATENT DOCUMENTS

| | | | |
|---|---|---|---|
| 8105304 | 11/1981 | Netherlands | 128/346 |
| 2036561 | 7/1980 | United Kingdom | 128/346 |

*Primary Examiner*—Dalton L. Truluck
*Attorney, Agent, or Firm*—Woodard, Emhardt, Naughton, Moriarty & McNett

[57] ABSTRACT

The incontinence control device of the present invention as described includes a cloth strap adapted to encircle a penis, the strap having cooperative pressure adherence layers on portions of the inner and outer surfaces so that the strap can form a circumference when the inner adherence layer is engaged with the outer adherence layer of the strap. The inner surface of the strap also has a compressible pad adjacent the pressure adherence layer and another compressible pad in fixed relation to the first pad. An inflatable sac is affixed to the strap between the two compressible pads. A tube passes through the strap to communicate with the interior of the inflatable sac at one end of the tube. A check valve is attached at the other end of the tube. A syringe is adapted to engage the check valve so that air in the syringe can be injected through the tube into the sac to inflate the sac. In the inflated condition, the sac and incontinence control device are adapted to impinge the urethra within the penis to, thereby, restrict the flow of urine through the urethra. The sac has a predetermined free shape with a height greater than the thickness of the two compressible pads so that the sac will maintain contact with the penis even when the sac is not inflated to ensure that the strap will not slip.

7 Claims, 2 Drawing Sheets

EXTERNAL STRAP INCONTINENCE CONTROL DEVICE

RFEFERENCE TO RELATED APPLICATION

This invention is a continuation in part of patent application Ser. No. 926,955, filed on Nov. 4, 1986.

BACKGROUND OF THE INVENTION

This invention relates generally to an apparatus for controlling urinary incontinence.

Urinary incontinence is a long-recognized medical condition posing a serious and embarrassing problem to those persons whose natural urethral valve or sphincter is no longer capable of controlling the flow of urine from the bladder. This problem can be the result of surgery, disease, neurological dysfunction, malformation of the urethral valve, and the natural physical deterioration accompanying advanced age. Solutions to the problem of urinary incontinence are many and are typically uncomfortable, unsanitary, inconvenient, offensive, inadequate, or unreliable.

Devices to control urinary incontinence include a pad of absorbent material to absorb all fluid that involuntarily escapes the bladder. Another method is to insert a catheter into the urinary tract with an exterior sealed collecting bag connected to the catheter tube. Artificial urethral valves represent yet another solution to the problem of urinary incontinence. In this type of device, the function of the urethral valve, or sphincter, is assumed by a mechanical valve of a variety of designs. Kwan-Gett et al., U.S. Pat. No. 3,768,102, proposes an implantable movable valve occluding means held in position by a spring calibrated to allow the valve to open when overcome by sufficient pressure from the bladder contents. The sprung valve remains open while under the normal flow of fluid from the bladder. Other patents disclose similarly sophisticated mechanical and magnetic urethral valve devices, such as Osthagen et al., U.S. Pat. No. 3,642,004; Osthagen et al., U.S. Pat. No. 3,503,400; Trick, U.S. Pat. No. 4,419,985.; Cornwell, U.S. Pat. No. 4,457,299; and Isaacson, U.S. Pat. No. 3,812,841.

Penile clamps for human males are another management technique whereby the clamp exerts pressure against the urethra to prevent outflow of fluid.

One object of the present invention is to provide a reliable device for male urinary incontinence control. Another object is to provide a device that has few movable parts and that is easily operable by the patient. Yet another object of the present invention is to provide an apparatus that is resistant to mechanical failure or accidental leakage. Other objects of this invention will become apparent to one skilled in the art through the accompanying disclosure and claims.

SUMMARY OF THE INVENTION

One embodiment of the device of the present invention might include a strap adapted to encircle a penis, the strap having cooperative pressure adherence layers on portions of the inner and outer surfaces. The inner surface of the strap also has a pair of compressible pads mounted thereon with an inflatable sac mounted between the compressible pads. Means for introducing a fluid into the elastic sac is provided to inflate the sac during use. The inflatable sac is located so as to impinge the urethra when the sac is encircled about the penis in its inflated condition. The sac has a predetermined free shape with a height when not inflated that is greater than the thickness of the compressible pads, so that when the sac is not inflated it remains in contact with the penis to prevent slippage.

DESCRIPTION OF THE PREFERRED EMBODIMENT

Figure 1:
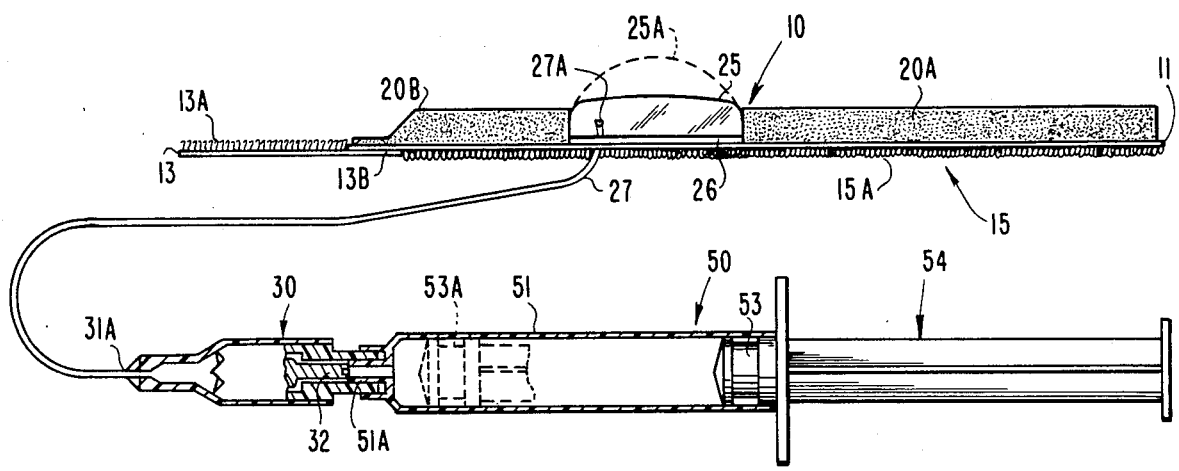
FIG. 1 is a side elevational view of an external strap incontinence control device according to one embodiment of the present invention, with a portion of the valve and syringe cutaway.
Figure 2:
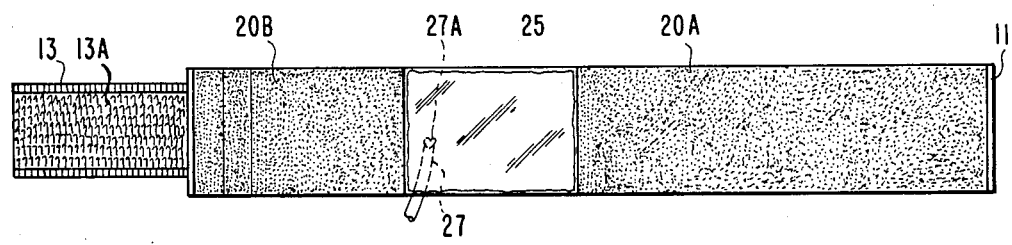
FIG. 2 is a top elevational view of a portion of the device shown in FIG. 1.

For the purposes of promoting an understanding of the principles of the invention. reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As contemplated in one embodiment of the present invention, the external strap incontinence control device consists of a strap assembly 10, a valve assembly 30 and a pump assembly 50 as illustrated in FIG. 1. The strap assembly comprises a flexible, non-extensible strap 11, preferably composed of a cloth material. A compressible foam pad 20A is affixed to the inner surface of strap 11 at one end of the strap. An inflatable sac 25 is affixed to the inner surface immediately adjacent foam pad 20A, and a second foam pad 20B is attached to the inner surface immediately adjacent sac 25. Sac 25 is capable of assuming an inflated shape 25A when filled with a fluid, typically air, under pressure. Sac 25 is preferably composed of a vinyl plastic material or other material suitable for contact with human skin.

Figure 3:
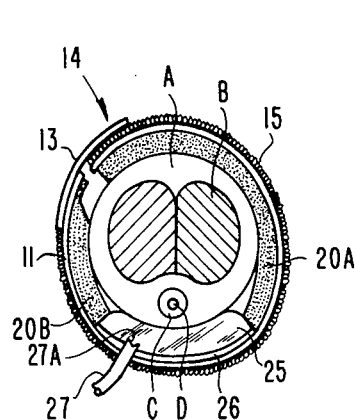
FIG. 3 is a cross-sectional view of a portion of the device shown in FIG. 1, shown encircling a penis with the inflatable sac in the deflated condition.

A strip 13 is attached to the exterior of strap 11 at location 13B at one end of the strap. The inner surface of strip 13 has a plurality of stiff hooked threads 13A that cover the exposed length of the strip and are immediately adjacent the free end of foam pad 20B. A pile 15, composed of a plurality of loops 15A of soft thread, covers substantially the length of the exterior of strap 10. In the normal position encircling the penis, as shown in FIG. 3, strip 13 overlies a portion of pile 15 at location 14. By application of pressure, hooked threads 13A engage loops 15A, and lock the strip and pile in firm engagement. This type of pressure-adhesive engagement can be of the type typically sold under the trade name "VELCRO".

A flexible tube 27 communicates air into inflatable sac 25 for inflation. The tube passes through pile 15 and strap 11 and the exit end 27A of the tube is sealed within sac 25. In this embodiment. exit end 27A is notched, as shown in FIG. 1 to maintain an air passage if sac 25 contacts and partially occludes exit end 27A. Inflatable sac 25 has a predetermined free shape so that it is slightly thicker than pads 20A and 20B. Sac 25 includes a floor portion 26 that is bonded to strap 11 in the preferred embodiment.

A valve assembly 30 is engaged at the feed end of tube 27 at location 31A. as shown in FIG. 1. In one embodiment, valve assembly 30 is a check valve, such as the valve described in the patent to Maskal et al., U.S. Pat. No. 3,831,629. In this embodiment, air enters or exits valve assembly 30 only when a plug 32 is depressed, such as when contacted by the exit nozzle 51A of a hypodermic syringe assembly 50. The check valve may also be replaced by a one-way valve assembly that is engaged to tube 27 during inflation and disengaged from the tube when air is released. The air is released from the tube and inflated sac by disengaging the valve assembly from feed end 31A of the tube.

In said one embodiment, air is injected through valve assembly 30 into tube 27 and inflatable sac 25 by way of a syringe assembly 50. The syringe assembly 50 has an exit nozzle 51A engaged with the valve assembly as shown in FIG. 1. The chamber 51 of the syringe assembly has a volume larger than the expanded volume of the sac when it is in its expanded state 25A. A plunger 53, having a stem 54, is slidingly engaged within chamber 51. Air is drawn into chamber 51 when the plunger is at the end of the chamber shown in FIG. 1. Air is forced out of the chamber by the plunger when it is pushed toward exit nozzle 51A to position 53A. The syringe described in this embodiment can be the typical plastic syringe in wide use within the medical community.

Figure 4:
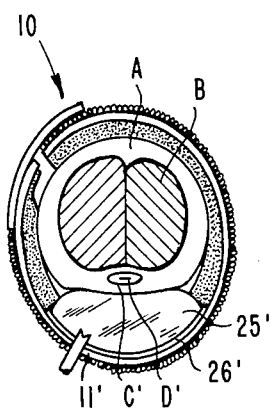
FIG. 4 is a cross-sectional view of the device as situated in FIG. 3, shown with the inflatable sac in the inflated condition to constrict the urethra.

The use of this incontinence control device is demonstrated with reference to FIGS. 3 and 4. Strap 11 is wrapped around the penis A and is held in this position at location 14 by the pressure adhesive VELCRO sections on the inner surface of strip 13 and the outer surface of strap 11 Inflatable sac 25 is positioned directly adjacent the corpus spongiosum C and urethra D. When sac 25 is not inflated, its predetermined shape allows it to maintain contact with penis A so that it cannot slip. In other words, the sac 25 always returns to a shape as illustrated in solid lines in FIG. 1 when the internal pressure is atmospheric. That is, the sac does not get thinner than the adjacent compressible pad. In this uninflated state, almost no pressure is exerted against the urethra D that might impede urination. Foam pads 20A and 20B are in contact with a large part of the remainder of the circumference of the penis and adjacent the corpora cavernosa B. The length of tube 27 and, consequently, the location of valve assembly 30 can be left to the discretion of the user after considering comfort, accessibility and ease of use.

FIG. 4 illustrates the normal configuration of device 10 to prevent the flow of urine from the urethra. Sac 25' is inflated, thereby applying pressure to the immediately adjacent portion of the penis A. The corpus spongiosum C' is, consequently, squeezed, holding the urethra D' closed. Once the sac has been inflated using syringe assembly 50, the syringe can be disengaged from valve assembly 30 and stored for later use. Check valve plug 32 will prevent air from escaping inflated sac 25'.

When urination is desired, the incontinence control device is in the condition shown in FIG. 3. Check valve plug 32 is depressed by exit nozzle 51A, allowing air to escape from sac 25 into chamber 51 until the sac assumes its predetermined shape. The pressure exerted against the corpus spongiosum C is relieved and the urethra D is opened, allowing urine to flow. Once urination is completed, the air in chamber 51 is injected back into the sac by depressing plunger 53. Once the sac has been inflated as in FIG. 4, the syringe can again be disengaged and plug 32 will seal check valve 30.

Figure 5:
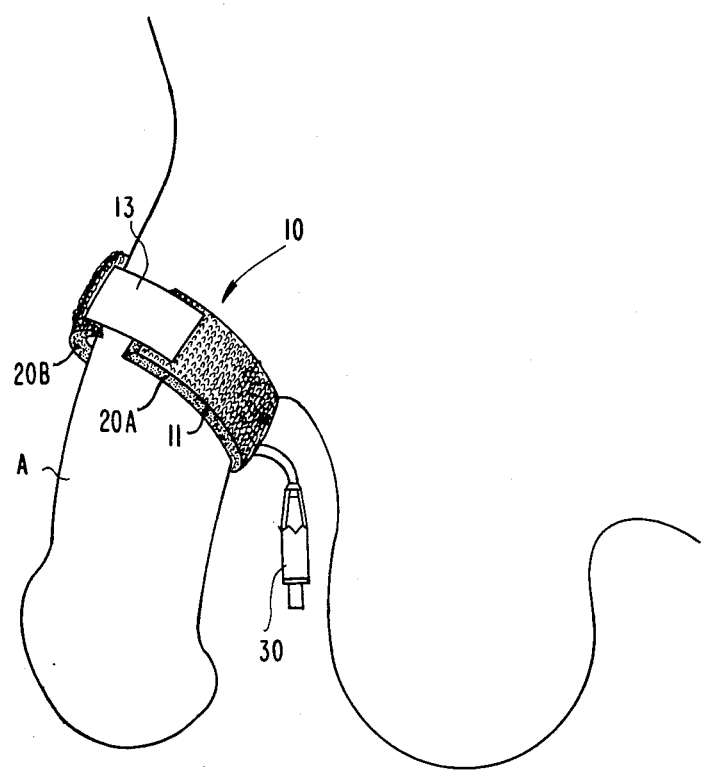
FIG. 5 is a side elevational view of the external strap incontinence control device as normally worn around the penis.

The exterior strap incontinence control device of this invention is sufficiently compact to avoid embarrassment or appear obvious from external appearances. Another advantage of this invention is that device 10 is not bulky or uncomfortable to wear. The device is normally worn about the base of the penis, as shown in FIG. 5. A short tube 27 can be used so that the valve assembly 30 resides near the penis, or a longer tube can be used to locate the valve assembly remote from the penis. Foam pads 20A and 20B contact the majority of the circumference of the penis to provide a comfortable, non-irritating interface with the device. It is understood that other arrangements of the foam pad and the inflatable sac are contemplated, such as a single foam pad extending over most of the inner surfaoe of the strap with the inflatable sac positioned at one end of the strap.

When sac 25 is in its normally inflated position (25' in FIG. 4) to restrict urine flow, the majority of the pressure exerted by the sac is absorbed by the portion of the penis immediately adjacent the urethra. The remaining portions of the penis endure little pressure so that the blood vessels in the corpora cavernosa B are not constricted. When the sac is in its inflated condition 25', floor 26 distends to condition 26' in which portion 11' of strap 11 bulges away from penis A. This allows some of the pressure exerted by inflated sac 25' to be diverted from the penis to further reduce the pressure experienced by the corpora cavernosa B. Moreover, if the sac is overinflated, floor 26' distends further to prevent overcompressing the corpus spongiosum D' and the adjacent portion of the penis. The arrangement of foam pads and inflatable sac of the present embodiment insures that incontinence control device 10 can be worn with minimal discomfort and with little risk of disturbing blood flow throughout the penis.

The mode of operation of the device, involving check valve 30 and syringe assembly 50, is simple and reliable. The device is mechanically simple so that there exists little chance of malfunction and accidental discharge of urine. This mechanical simplicity also renders this device easy and cost-efficient to produce.

Figure 6:
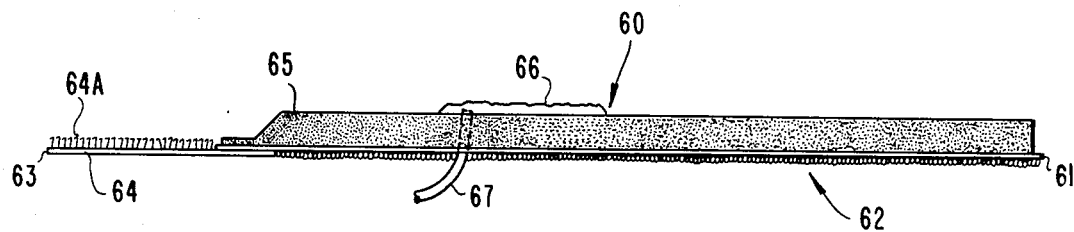
FIG. 6 is a side elevational view of a portion of an external strap incontinence device according to a second embodiment of the present invention.

In a second embodiment of the present invention, illustrated in FIG. 6, incontinence control device 60 comprises a strap 61 with a pile 62 over most of the length of the strap. A strip 63 is affixed at one end of the strap having a plurality of hooks 64A on its inner surface 64. To this extent, device 60 is similar to device 10 of the first embodiment. However, in this second embodiment, a foam pad 65 extends over substantially the entire length of strap 61.

Inflatable sac 66 is mounted directly on foam pad 65. In this embodiment, sac 66 does not have a predetermined shape since it will always be in contact with the penis, even when deflated, being mounted on the foam pad rather than between pads having a certain thickness. In the former embodiment, the predetermined shape was needed to prevent the sac from deflating to a thickness less than the thickness of the adjacent pads. The contact between the penis and the inflatable sac, which is typically composed of a vinyl or other plastic, is important to keep the device from sliding along the penis. In the present embodiment, the placement of sac 66 atop pad 65 insures this contact between the sac and the penis.

Sac 66 is fed by a flexible tube 67 that passes through the pile 62, strap 61 and foam pad 65. Valving arrangements, such as those discussed in connection with the first embodiment, can be used with device 60 of the second embodiment.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A male incontinence control device, comprising:

an elongated flexible inextensible strap adapted to encircle a penis in an overlapping arrangement, said strap having an outer surface and an inner surface;

said outer surface having a first pressure adherence layer over substantially the entire length of said outer surface and a coupling strip affixed thereon at one end of said strap, said coupling strip having a second pressure adherence layer, said first and second pressure adherence layers being detachably adherent to each other when said strap is encircled about a penis in said overlapping arrangement;

said inner surface, facing the penis when said strap is encircled thereabout, having affixed thereon a first compressible pad adjacent said one end and a second compressible pad spaced from said first pad and extending to the other end of said strap;

an inflatable vinyl sac having a floor portion and a bubble portion, said floor portion being adhered to said inner surface between said first and second pads, said bubble portion being sized to contact only the region of the penis immediately adjacent the urethra and having a predetermined free noninflated shape with a height from said inner surface greater than the thickness of said first and second pads;

means for inflating said sac including an inflation tube communicating with the interior of said sac in sealing engagement at its one end with said floor portion of sac and passing through an opening in said strap, said inflation means further including a check valve sealingly engaged at the other end of said inflation tube; wherein, said sac, when inflated, reacts between said strap and the penis to constrict the urethra and coacts with said compressible pads to limit the pressure exerted by said strap against the remainder of the penis; and wherein said floor portion elastic so that when said sac is inflated said floor portion distends slightly to further reduce the pressure exerted by said strap against the remainder of the penis.

2. A male incontinence control device comprising:

an elongated flexible inextensible strap adapted to encircle a penis in an overlapping arrangement, said strap having an outer surface and an inner surface;

said outer surface having a first pressure adherence layer over substantially the entire length of said outer surface and a coupling strip affixed thereon at one end of said strap, said coupling strip having a second pressure adherence layer, said first and second pressure adherence layers being detachably adherent to each other when said strap is encircled about a penis in said overlapping arrangement;

said inner surface further having a compressible pad immediately adjacent said one end and extending over substantially the entire length of said strap;

an inflatable sac mounted onto a segment of said compressible pad, said sac being sized to contact only the region of the penis immediately adjacent the urethra; and means for inflating said sac including an inflation tube communicating with the interior of said sac in sealing engagement at its one end with said sac and passing through an opening in said strap and said compressible pad, said inflation means further including a check valve sealingly engaged at the other end of said inflation tube;

wherein said inflation tube includes an opening at its one end, with a notch in the tube wall at said opening to maintain a fluid passageway through said tube if said sac should cover said opening; and further wherein, when said sac is inflated said segment of said compressible pad onto which said sac is mounted compresses to limit the pressure exerted by said strap against the remainder of the penis.

3. The male incontinence control device according to claim 1 or claim 2, wherein said means for inflating includes said check valve being adapted to removably engage a hypodermic syringe and being operable to allow a fluid to pass therethrough to inflate or deflate said sac only when engaged with said syringe, and to prevent fluid leakage from said sac otherwise.

4. The male incontinence control device according to claim 1, wherein said inflation tube includes an opening at its one end, with a notch in the tube wall at said opening to maintain a fluid passageway through said tube if said sac should cover said opening.

5. The male incontinence control device according to claim 1 or claim 2, wherein said strap is composed of a cloth material.

6. The male incontinence control device according to claim 1, wherein said strap is of sufficient length so that no part of said strap overlaps either of said compressible pads when said strap encircles a penis in said overlapping arrangement.

7. The male incontinence control device according to claim 2, wherein said strap is of sufficient length so that no part of said strap overlaps said compressible pad when said strap encircles a penis in said overlapping arrangement.

* * * * *